(12) United States Patent
Abe et al.

(10) Patent No.: US 7,794,876 B2
(45) Date of Patent: Sep. 14, 2010

(54) PENTAFLUOROPHENYLOXY COMPOUND, AND NONAQUEOUS ELECTROLYTE SOLUTION AND LITHIUM SECONDARY BATTERY USING SAME

(75) Inventors: Koji Abe, Ube (JP); Takaaki Kuwata, Ube (JP); Manabu Takase, Ube (JP)

(73) Assignee: Ube Industries, Ltd., Ube-shi (JP)

( * ) Notice: Subject to any disclaimer, the term of this patent is extended or adjusted under 35 U.S.C. 154(b) by 581 days.

(21) Appl. No.: 11/632,840

(22) PCT Filed: Nov. 8, 2006

(86) PCT No.: PCT/JP2006/022285

§ 371 (c)(1),
(2), (4) Date: Mar. 1, 2007

(87) PCT Pub. No.: WO2008/056413

PCT Pub. Date: May 15, 2008

(65) Prior Publication Data

US 2008/0107969 A1 May 8, 2008

(51) Int. Cl.
*H01M 6/04* (2006.01)
(52) U.S. Cl. .................. 429/199; 429/200; 429/327; 429/326; 429/324; 429/330; 429/336; 429/332; 429/188; 252/62.2
(58) Field of Classification Search .......... 429/199, 429/200, 327, 326, 324, 330, 336, 332, 188; 252/62.2
See application file for complete search history.

(56) References Cited

U.S. PATENT DOCUMENTS

| 7,261,975 B2 * | 8/2007 | Abe et al. ............ 429/199 |
| 7,297,442 B2 * | 11/2007 | Abe et al. ............ 429/199 |
| 2005/0255384 A1 | 11/2005 | Abe et al. | |

FOREIGN PATENT DOCUMENTS

| EP | 1 672 729 A1 | 6/2006 |
| JP | 39-5943 | 4/1964 |
| WO | WO 03/077351 A1 | 9/2003 |
| WO | WO 2005/029631 | 3/2005 |

OTHER PUBLICATIONS

An abstract of US 7,297,442 cited in a search report. No date.*
Nimesh R. Patel, et al., "Per- and Polyfluoroaryl Mono-and Disiloxanes as Transfer Reagents in the Synthesis of Highly Fluorinated Mono-and Diethers", Inorganic Chemistry, vol. 34, No. 1, 1995, pp. 13-17.
Jarod M. Younker, et al., "A Mechanistic Study of the Alkaline Hydrolysis of Diaryl Sulfate Diesters", J. Org. Chem., vol. 69, No. 26, 2004, pp. 9043-9048.

* cited by examiner

*Primary Examiner*—Laura S Weiner
(74) *Attorney, Agent, or Firm*—Oblon, Spivak, McClelland, Maier & Neustadt, L.L.P.

(57) ABSTRACT

To provide a novel pentafluorophenyloxy compound, a method for producing same, a nonaqueous electrolyte solution capable of forming a lithium secondary battery having excellent battery characteristics such as electrical capacity, cycling property and storage property, and a lithium secondary battery.

A pentafluorophenyloxy compound represented by the general formula (I) shown below, a method for producing same, a nonaqueous electrolyte solution containing same and a lithium secondary battery:

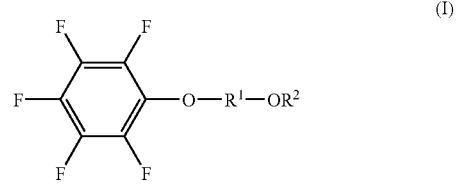

wherein $R^1$ represents a —COCO— group, a S=O group or a $S(=O)_2$ group, $R^2$ represents an alkyl group, a cycloalkyl group, an alkenyl group, an alkynyl group, an aryl group or an aralkyl group with the proviso that at least one of the hydrogen atoms of $R^2$ may be each substituted with a halogen atom and that $R^2$ does not represent an aryl group when $R^1$ represents a —COCO— group.

14 Claims, No Drawings

PENTAFLUOROPHENYLOXY COMPOUND, AND NONAQUEOUS ELECTROLYTE SOLUTION AND LITHIUM SECONDARY BATTERY USING SAME

TECHNICAL FIELD

The present invention relates to a novel pentafluorophenyloxy compound useful as an intermediate raw material for various materials or as a battery material, to a method for producing same, and to a nonaqueous electrolyte solution and a lithium secondary battery containing same.

BACKGROUND ART

In recent years, lithium secondary batteries have been widely used as power supplies for driving small electronic devices and the like. Such lithium secondary batteries are mainly constituted of a positive electrode comprised of a lithium compound oxide, a negative electrode comprised of a carbon material or a lithium metal, and a nonaqueous electrolyte solution. As the nonaqueous electrolyte solution, a carbonate such as ethylene carbonate (EC) or propylene carbonate (PC) is used.

A lithium secondary battery using, for example, $LiCoO_2$, $LiMn_2O_4$ or $LiNiO_2$ as a positive electrode brings about a reduction of the battery performance, when a part of the solvent of the nonaqueous electrolyte solution locally undergoes an oxidative decomposition during the charging, because the decomposition products inhibit the desired electrochemical reaction of the battery. Such a reduction is considered to be attributed to an electrochemical oxidation of the solvent at the interface between the positive electrode material and the nonaqueous electrolyte solution.

Also, a lithium secondary battery using, for example, a highly crystallized carbon material, such as natural graphite or artificial graphite, as a negative electrode brings about a reduction of the battery performance, when the solvent of the nonaqueous electrolyte solution undergoes a reductive decomposition on the surface of the negative electrode during the charging. Even in the case of EC which is generally used as a solvent for the nonaqueous electrolyte solution, a part thereof undergoes a reductive decomposition during repeated charging and discharging.

As techniques for improving the battery characteristics of such lithium secondary batteries, there are known, for example, Patent Documents 1 to 6.

Patent Document 1 discloses a lithium secondary battery using a pentafluorobenzene compound, such as pentafluoroanisole, having an electron donating group. The coin battery shows a discharge capacity retentivity of about 80% after 200 cycles and, therefore, the cycle property is not satisfactory.

Patent Document 2 discloses that pentafluoroanisole is usable as an oxidation reduction reagent as means for protecting from chemical overcharging of nonaqueous electrolyte solution secondary battery but does not mention the cycling property thereof.

Patent Document 3 suggests a nonaqueous electrolyte solution containing 2-propynyl phenyl carbonate, while Patent Document 4 suggests a nonaqueous electrolyte solution containing 2-propynyl phenyl oxalate.

Patent Document 5 discloses in its Example 5 a nonaqueous electrolyte solution containing pentafluorophenyl methyl carbonate, while Patent Document 6 discloses a nonaqueous electrolyte solution containing pentafluorophenylmethane sulfonate as well as vinylene carbonate and/or 1,3-propane sultone.

In these nonaqueous electrolyte solutions, the battery characteristics are improved in a certain degree. However, there is an increasing demand for higher capacity and longer cycle life. Therefore, further improvement of battery characteristics is required.

Patent Document 1: U.S. Patent Application Publication No. 2002/110735
Patent Document 2: Japanese Unexamined Patent Publication No. H07-302614
Patent Document 3: Japanese Unexamined Patent Publication No. 2000-195545
Patent Document 4: Japanese Unexamined Patent Publication No. 2002-124297
Patent Document 5: International Publication No. 03/77351
Patent Document 6: International Publication No. 05/29631

DISCLOSURE OF INVENTION

It is the object of the present invention to provide a novel pentafluorophenyloxy compound useful as an intermediate raw material for various materials or as a battery material, a method for producing same, a nonaqueous electrolyte solution capable of forming a lithium secondary battery having excellent battery characteristics such as electrical capacity, cycling property and storage property, and a lithium secondary battery.

The present inventors have synthesized a novel pentafluorophenyloxy compound, such as pentafluorophenyl methyl oxalate, and found that a lithium secondary battery having excellent cycling property, etc. can be provided by using a nonaqueous electrolyte solution in which the novel compound is contained. The present invention has been completed based on the above finding.

Thus, the present invention provides the following items (1) to (4):

(1) A pentafluorophenyloxy compound represented by the following general formula (I):

[Chemical formula 1]

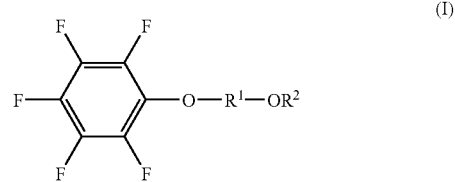

wherein $R^1$ represents a —COCO— group, a S=O group or a $S(=O)_2$ group, $R^2$ represents a $C_1$ to $C_{12}$ alkyl group, a $C_3$ to $C_{12}$ cycloalkyl group, a $C_2$ to $C_{12}$ alkenyl group, a $C_3$ to $C_{12}$ alkynyl group, a $C_6$ to $C_{18}$ aryl group or a $C_7$ to $C_{20}$ aralkyl group with the proviso that at least one of the hydrogen atoms of $R^2$ may be each substituted with a halogen atom and that $R^2$ does not represent an aryl group when $R^1$ represents a —COCO— group.

(2) A method of producing a pentafluorophenyloxy compound represented by the above general formula (I), comprising reacting pentafluorophenol with an acid halide represented by the general formula $R^2O$—$R^1$—X (where X represents a halogen atom and $R^1$ and $R^2$ are the same as above) or a thionyl halide in the presence of a base.

(3) A nonaqueous electrolyte solution, in which an electrolyte salt is dissolved in a nonaqueous solvent, the nonaqueous electrolyte solution comprising a pentafluorophenyloxy compound in an amount of 0.01 to 10% by weight based on the weight of the nonaqueous electrolyte solution, the pentafluorophenyloxy compound being represented by the following general formula (II) or (III):

[Chemical formula 2]

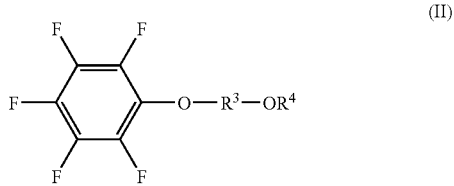

wherein $R^3$ represents a —COCO— group, a C=O group, a S=O group or a S(=O)$_2$ group, $R^4$ represents a $C_1$ to $C_{12}$ alkyl group, a $C_3$ to $C_{12}$ cycloalkyl group, a $C_2$ to $C_{12}$ alkenyl group, a $C_3$ to $C_{12}$ alkynyl group, a $C_6$ to $C_{18}$ aryl group or a $C_7$ to $C_{20}$ aralkyl group with the proviso that at least one of the hydrogen atoms of $R^4$ may be each substituted with a halogen atom and that $R^4$ represents a $C_2$ to $C_{12}$ alkenyl group or a $C_3$ to $C_{12}$ alkynyl group when $R^3$ represents a C=O group,

[Chemical formula 3]

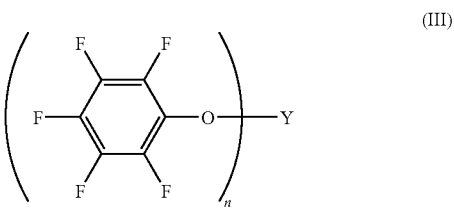

wherein Y represents an alkali metal or an alkaline earth metal and n is 1 or 2.

(4) A lithium secondary battery comprising a positive electrode, a negative electrode, and a nonaqueous electrolyte solution which includes an electrolyte salt dissolved in a nonaqueous solvent, the nonaqueous electrolyte solution comprising a pentafluorophenyloxy compound in an amount of 0.01 to 10% by weight based on the weight of the nonaqueous electrolyte solution, the pentafluorophenyloxy compound being represented by the above general formula (II) or (III).

BEST MODE FOR CARRYING OUT THE INVENTION

[Novel Pentafluorophenyloxy Compound]

A novel pentafluorophenyloxy compound according to the present invention is represented by the following general formula (I):

[Chemical formula 4]

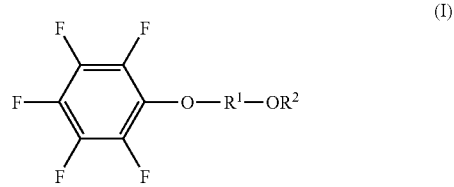

wherein $R^1$ represents a —COCO— group, a S=O group or a S(=O)$_2$ group, $R^2$ represents a $C_1$ to $C_{12}$ alkyl group, a $C_3$ to $C_{12}$ cycloalkyl group, a $C_2$ to $C_{12}$ alkenyl group, a $C_3$ to $C_{12}$ alkynyl group, a $C_6$ to $C_{18}$ aryl group or a $C_7$ to $C_{20}$ aralkyl group with the proviso that at least one of the hydrogen atoms of $R^2$ may be each substituted with a halogen atom and that $R^2$ does not represent an aryl group when $R^1$ represents a —COCO— group.

As the $C_1$ to $C_{12}$ alkyl group of $R^2$ in the general formula (I), there may be mentioned a methyl group, an ethyl group, a propyl group, a butyl group, a pentyl group, a hexyl group, a heptyl group, an octyl group, a nonyl group, a decyl group, a dodecyl group, etc. Among these, $C_1$ to $C_6$ alkyl groups are preferred. Particularly preferred are $C_1$ to $C_4$ alkyl groups such as a methyl group, an ethyl group, a propyl group, a butyl group, etc. These alkyl groups may be branched alkyl groups such as an isopropyl group and a tert-butyl group.

As the $C_3$ to $C_{12}$, preferably $C_3$ to $C_7$ cycloalkyl group, there may be mentioned a cyclopropyl group, a cyclohexyl group, etc. As the $C_2$ to $C_{12}$, preferably $C_2$ to $C_6$ alkenyl group, there may be mentioned a vinyl group, a 2-propenyl group, a 2-butenyl group, a 3-butenyl group, a 4-pentenyl group, etc. As the $C_3$ to $C_{12}$, preferably $C_3$ to $C_7$ alkynyl group, there may be mentioned a 2-propynyl group, 2-butynyl group, a 3-butynyl group, a 4-pentynyl group, a 5-hexynyl group, etc. As the $C_6$ to $C_{18}$ aryl group, there may be mentioned a pentafluorophenyl group, a heptafluoronaphthyl group, a perfluorobiphenyl group, etc. As the $C_7$ to $C_{20}$ aralkyl group, there may be mentioned a benzyl group, a trityl group, etc.

Preferable examples of the compounds in which $R^1$ is a —COCO— group include pentafluorophenyl methyl oxalate, pentafluorophenyl ethyl oxalate, pentafluorophenyl butyl oxalate and pentafluorophenyl cyclohexyl oxalate.

Among these, pentafluorophenyl methyl oxalate and pentafluorophenyl ethyl oxalate, which have an alkyl group, are preferred from the standpoint of applicability to various substances and materials.

Preferable examples of the compounds in which $R^1$ is a S=O group include pentafluorophenyl methyl sulfite, pentafluorophenyl ethyl sulfite, pentafluorophenyl butyl sulfite, pentafluorophenyl cyclohexyl sulfite, 2-propenyl pentafluorophenyl sulfite, 2-propynyl pentafluorophenyl sulfite and bis(pentafluorophenyl) sulfite.

Among these, pentafluorophenyl methyl sulfite, pentafluorophenyl ethyl sulfite, 2-propynyl pentafluorophenyl sulfite and bis(pentafluorophenyl) sulfite are preferred from the standpoint of applicability to various substances and materials.

Preferable examples of the compounds in which $R^1$ is a S(=O)$_2$ group include pentafluorophenyl methyl sulfate, pentafluorophenyl ethyl sulfate, pentafluorophenyl butyl sulfate, pentafluorophenyl cyclohexyl sulfate, 2-propenyl pentafluorophenyl sulfate, 2-propynyl pentafluorophenyl sulfate and bis(pentafluorophenyl) sulfate.

Among these, pentafluorophenyl methyl sulfate, pentafluorophenyl ethyl sulfate and bis(pentafluorophenyl) sulfate are preferred from the standpoint of applicability to various substances and materials.

[Method for Producing Novel Pentafluorophenyloxy Compound]

Although a method for producing the pentafluorophenyloxy compound represented by the general formula (I) is not specifically limited, such a compound may be efficiently produced according to a method of the present invention. That is, it is preferred that pentafluorophenol be reacted with an acid halide represented by the general formula $R^2O$—$R^1$—X (where X represents a halogen atom and $R^1$ and $R^2$ are the same as above) or a thionyl halide in the presence of a base.

As the acid halide represented by the general formula $R^2O$—$R^1$—X, an acid chloride represented by the general formula $R^2O$—$R^1$—Cl is preferred. Preferable examples of the acid chloride include methyl chloroglyoxylate, ethyl chloroglyoxylate, propynyl chloroglyoxylate and propynyl chloroformate, for example. As the thionyl halide, thionyl chloride is preferred.

In the above reaction, the acid halide or thionyl halide is generally used in an amount of 0.5 to 2 moles, preferably 0.8 to 1.5 moles, per mole of pentafluorophenol.

As the base used in the method of the present invention, there may be mentioned amines such as pyridine, picoline, lutidine, dimethylaminopyridine, trimethylamine, triethylamine and diisopropylethylamine; alkali metal carbonates such as potassium carbonate, sodium carbonate and sodium hydrogen carbonate; alkali metal hydroxides such as sodium hydroxide and potassium hydroxide; alkaline earth metal hydroxides such as calcium hydroxide; and alkali metal alkoxides such as sodium methoxide, sodium ethoxide and potassium tert-butoxide. Above all, amines such as pyridine, picoline and triethylamine are particularly preferred.

The base is generally used in an amount of 0.01 to 0.2 mole, preferably 0.02 to 0.15 mole, per mole of the pentafluorophenol. The reaction is preferably carried out in a solvent such as a halogenated hydrocarbon, e.g. dichloromethane, dichloroethane or chloroform; an aromatic hydrocarbon, e.g. benzene or toluene; or an ether, e.g. diethyl ether, tetrahydrofuran or dioxane.

The reaction temperature is generally −10° C. to 80° C., preferably −5° C. to 50° C., particularly preferably 0° C. to 40° C.

[Nonaqueous Electrolyte Solution]

The nonaqueous electrolyte solution of the present invention is characterized in that a pentafluorophenyloxy compound represented by the general formula (II) or (III) shown below is contained in a nonaqueous electrolyte solution in which an electrolyte salt is dissolved in a nonaqueous solvent:

[Chemical formula 5]

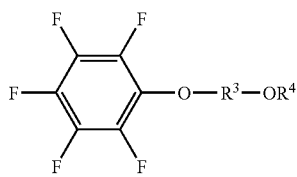

(II)

wherein, $R^3$ represents a —COCO— group, a C=O group, a S=O group or a S(=O)$_2$ group, $R^4$ represents a $C_1$ to $C_{12}$ alkyl group, a $C_3$ to $CO_2$ cycloalkyl group, a $C_2$ to $C_{12}$ alkenyl group, a $C_3$ to $C_{12}$ alkynyl group, a $C_6$ to $C_{18}$ aryl group or a $C_7$ to $C_{20}$ aralkyl group with the proviso that at least one of the hydrogen atoms of $R^4$ may be each substituted with a halogen atom and that $R^4$ represents a $C_2$ to $C_{12}$ alkenyl group or a $C_3$ to $C_{12}$ alkynyl group when $R^3$ represents a C=O group,

[Chemical formula 6]

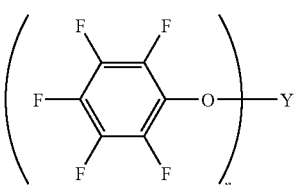

(III)

wherein Y represents an alkali metal or an alkaline earth metal and n is 1 or 2.

In the nonaqueous electrolyte solution of the present invention, when the content of the pentafluorophenyloxy compound represented by the general formula (II) or (III) is excessively high, the battery characteristics may occasionally deteriorated. When the content is excessively low, on the other hand, the desired satisfactory battery characteristics may not be obtained. Therefore, the content of the pentafluorophenyloxy compound is preferably at least 0.01% by weight, more preferably at least 0.1% by weight, most preferably at least 0.3% by weight, based on the weight of the nonaqueous electrolyte solution. The upper limit of the content is preferably not greater than 10% by weight, more preferably not greater than 5% by weight, most preferably not greater than 3% by weight, based on the weight of the nonaqueous electrolyte solution.

As $R^3$ in the general formula (II), a —COCO— group, a C=O group or a S=O group is preferred from the standpoint of improved battery characteristics such as cycling property. Particularly preferred is a —COCO— group or a S=O group.

$R^4$ in the general formula (II) may be a fluorophenyl group or a pentafluorophenyl group in which at least one of the hydrogen atoms of $R^4$ is substituted with a halogen atom such as a fluorine atom or a chlorine atom. When $R^3$ is a C=O group, $R^4$ is a $C_2$ to $C_{12}$, preferably $C_3$ to $C_6$ alkenyl group or a $C_3$ to $C_{12}$, preferably $C_3$ to $C_7$ alkynyl group.

As the $C_1$ to $C_{12}$, preferably $C_1$ to $C_6$ alkyl group, the $C_3$ to $C_{12}$ preferably $C_3$ to $C_7$ cycloalkyl group, the $C_2$ to $C_{12}$ preferably $C_2$ to $C_6$ alkenyl group, the $C_3$ to $C_{12}$ preferably $C_3$ to $C_7$ alkynyl group, which are represented by $R^4$, there may be mentioned those described above in connection with $R^2$ of the general formula (I).

As the $C_6$ to $C_{18}$ aryl group, there may be mentioned a phenyl group, a fluorophenyl group, a pentafluorophenyl group, etc. As the $C_7$ to $C_{20}$ aralkyl group, there may be mentioned a benzyl group, a trityl group, etc.

Preferable examples of the compound in which $R^3$ is a —COCO— group include pentafluorophenyl methyl oxalate, pentafluorophenyl ethyl oxalate, pentafluorophenyl butyl oxalate, pentafluorophenyl cyclohexyl oxalate, 2-propenyl pentafluorophenyl oxalate, 2-propynyl pentafluorophenyl oxalate, pentafluorophenyl phenyl oxalate, bis(pentafluorophenyl) oxalate and pentafluorophenyl benzyl oxalate.

Among these, pentafluorophenyl methyl oxalate and pentafluorophenyl ethyl oxalate, which have an alkyl group, and 2-propynyl pentafluorophenyl oxalate, which has an alkynyl group, are particularly preferred from the standpoint of improved battery characteristics such as cycling property.

Preferable examples of the compound in which $R^3$ is a C=O group include vinyl pentafluorophenyl carbonate, 2-propenyl pentafluorophenyl carbonate, 3-propenyl pentafluorophenyl carbonate, 2-propynyl pentafluorophenyl carbonate, 2-butynyl pentafluorophenyl carbonate, 3-butynyl pentafluorophenyl carbonate and 4-pentynyl pentafluorophenyl carbonate.

Among these, 2-propynyl pentafluorophenyl carbonate is particularly preferred from the standpoint of improved battery characteristics such as cycling property.

Preferable examples of the compound in which $R^3$ is a S=O group include pentafluorophenyl methyl sulfite, pentafluorophenyl ethyl sulfite, pentafluorophenyl butyl sulfite, pentafluorophenyl cyclohexyl sulfite, 2-propenyl pentafluorophenyl sulfite, 2-propynyl pentafluorophenyl sulfite, pentafluorophenyl phenyl sulfite, bis(pentafluorophenyl) sulfite and pentafluorophenyl benzyl sulfite.

Among these, pentafluorophenyl methyl sulfite, pentafluorophenyl ethyl sulfite, 2-propynyl pentafluorophenyl sulfite and bis(pentafluorophenyl) sulfite are preferred and bis(pentafluorophenyl) sulfite is particularly preferred from the standpoint of improved battery characteristics such as cycling property.

Preferable examples of the compound in which $R^3$ is a $S(=O)_2$ group include pentafluorophenyl methyl sulfate, pentafluorophenyl ethyl sulfate, pentafluorophenyl butyl sulfate, pentafluorophenyl cyclohexyl sulfate, 2-propenyl pentafluorophenyl sulfate, 2-propynyl pentafluorophenyl sulfate, pentafluorophenyl phenyl sulfate, bis(pentafluorophenyl) sulfate and pentafluorophenyl benzyl sulfate.

Among these, pentafluorophenyl methyl sulfate, pentafluorophenyl ethyl sulfate and bis(pentafluorophenyl) sulfate are particularly preferred from the standpoint of improved battery characteristics such as cycling property.

In the general formula (III), Y represents an alkali metal such as Li, Na and K or an alkaline earth metal such as Mg, Ca and Ba.

Preferable examples of the pentafluorophenyloxy compound represented by the general formula (III) include lithium pentafluorophenoxide, sodium pentafluorophenoxide, potassium pentafluorophenoxide, magnesium bispentafluorophenoxide, calcium bispentafluorophenoxide and barium bispentafluorophenoxide. Among these, lithium pentafluorophenoxide is particularly preferred from the standpoint of improved battery characteristics such as cycling property.

[Other Additives]

It is preferred that the nonaqueous electrolyte solution of the present invention contain at least one of vinylene carbonate (VC), 1,3-propane sultone (PS) and a triple bond-containing compound in addition to the pentafluorophenyloxy compound represented by the general formula (II) or (III) from the standpoint of improved charging and discharging characteristics.

When the content of vinylene carbonate and 1,3-propane sulfone is excessively high, the battery characteristics are occasionally reduced. When the content is excessively low, the desired battery characteristics are not obtainable. Thus, the content of vinylene carbonate is preferably not less than 0.1% by volume, more preferably not less than 0.5% by volume, most preferably not less than 1% by volume, based on the volume of the nonaqueous electrolyte solution. The upper limit of the content is preferably not more than 10% by volume, more preferably not more than 5% by volume, most preferably not more than 3% by volume, based on the volume of the nonaqueous electrolyte solution.

The content of 1,3-propane sultone is preferably not less than 0.1% by volume, more preferably not less than 0.5% by volume, most preferably not less than 1% by volume, based on the volume of the nonaqueous electrolyte solution. The upper limit of the content is preferably not more than 10% by volume, more preferably not more than 5% by volume, most preferably not more than 3% by volume, based on the volume of the nonaqueous electrolyte solution.

In a high capacity battery, the cycling property is generally deteriorated when the electrode mixture density is increased. However, a co-joint use of a triple bond-containing compound can improve the cycling property and, therefore, is preferred.

As the triple bond-containing compound, there may be mentioned methyl propargyl carbonate (MPC), ethyl propargyl carbonate (EPC), dipropargyl carbonate (DPC), dipropargyl oxalate (DPO), propargyl methanesulfonate, dipropargyl sulfite, methyl propargyl sulfite, ethyl propargyl sulfite, etc.

The content of the triple bond-containing compound is preferably not less than 0.01% by volume, more preferably not less than 0.1% by volume, most preferably not less than 0.5% by volume, based on the volume of the nonaqueous electrolyte solution. The upper limit of the content is preferably not more than 10% by volume, more preferably not more than 5% by volume, most preferably not more than 3% by volume, based on the volume of the nonaqueous electrolyte solution.

[Nonaqueous Solvent]

As the nonaqueous solvent used in the nonaqueous electrolyte solution of the present invention, there may be mentioned, for example, cyclic carbonates, linear carbonates, linear esters, ethers, amides, phosphoric acid esters, sulfones, lactones, nitriles, S=O containing compounds, etc.

As the cyclic carbonate, there may be mentioned ethylene carbonate (EC), propylene carbonate (PC), butylene carbonate, fluoroethylene carbonate, dimethylvinylene carbonate, vinyl ethylene carbonate, etc. Particularly, it is most preferred that the solvent contains EC having a high dielectric constant.

As the linear carbonate, there may be mentioned asymmetric linear carbonates such as methyl ethyl carbonate (MEC), methyl propyl carbonate, methyl butyl carbonate and ethyl propyl carbonate; and symmetric linear carbonates such as dimethyl carbonate (DMC), diethyl carbonate (DEC), dipropyl carbonate and dibutyl carbonate.

As the linear ester, there may be mentioned methyl propionate, methyl pivalate, butyl pivalate, hexyl pivalate, octyl pivalate, dimethyl oxalate, ethyl methyl oxalate and diethyl oxalate. As the ether, there may be mentioned tetrahydrofuran, 2-methyltetrahydrofuran, 1,4-dioxane, 1,2-dimethoxyethane, 1,2-diethoxyethane and 1,2-dibutoxyethane. There may be mentioned dimethylformamide as the amide; trimethyl phosphate and trioctyl phosphate as the phosphoric ester; divinylsulfone as the sulfone; γ-butyrolactone, γ-valerolactone and α-angelicalactone as the lactone; and acetonitrile and adiponitrile as the nitrile.

As the S=O containing compound, there may be mentioned 1,4-propane sultone, 1,4-butanediol dimethanesulfonate, glycol sulfite, propylene sulfite, glycol sulfate, propylene sulfate, dipropargyl sulfite, methyl propargyl sulfite, ethyl propargyl sulfite, didivinyl sulfone, etc.

The above-described nonaqueous solvents are generally used as a mixture to achieve appropriate properties. As examples of the combination, there may be mentioned various combinations such as a combination of a cyclic carbonate and a linear carbonate, a combination of a cyclic carbonate and a lactone, a combination of a lactone and a linear ester, a combination of a cyclic carbonate, a lactone and a linear ester, a combination of a cyclic carbonate, a linear carbonate and a lactone, a combination of cyclic carbonate and an ether, a combination of a cyclic carbonate, a linear carbonate and an ether, and a combination of a cyclic carbonate, a linear carbonate and a linear ester. The mixing ratio is not specifically limited.

Above all, a combination of cyclic carbonate and a linear carbonate is preferred. Specifically, a combination of a cyclic carbonate such as EC and PC and a linear carbonate such as MEC and DEC is particularly preferred. The proportion of the cyclic carbonate and the linear carbonate is preferably such that the volume ratio of the cyclic carbonate to the linear carbonate is 20:80 to 40:60, particularly preferably 25:75 to 35:65.

As the electrolyte salt used in the present invention, there may be mentioned, for example, $LiPF_6$, $LiBF_4$, $LiClO_4$, lithium salts having a linear alkyl group or groups such as $UN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3$ (iso- $C_3F_7)_3$ and $LiPF_5$ (iso-$C_3F_7$) and lithium salts having a cyclic alkylene group or groups such as $(CF_2)_2(SO_2)_2NLi$ and $(CF_2)_3(SO_2)_2NLi$.

Above all, particularly preferable electrolyte salts are $LiPF_6$, $LiBF_4$ and $LiN(SO_2CF_3)_2$ and the most preferable electrolyte salt is $LiPF_6$. These electrolyte salts may be employed singly or in combination of two or more thereof.

As the preferable combination of these electrolyte salts, there may be mentioned a combination of $LiPF_6$ and $LiBF_4$, a combination of $LiPF_6$ and $LiN(SO_2CF_3)_2$ and a combination of $LiBF_4$ and $LiN(SO_2CF_3)_2$. Particularly preferred is a combination of $LiPF_6$ and $LiBF_4$. The volume ratio of $LiPF_6$ to $LiBF_4$ is preferably 80:20 to 99:1, particularly preferably 90:10 to 98:2.

The electrolyte salts may be mixed at any arbitrary ratio. When $LiPF_6$ is used in combination with other electrolyte salts, the proportion (molar ratio) of said other electrolyte salts relative to all the electrolyte salts is preferably 0.01 to 45%, more preferably 0.03 to 20%, still more preferably 0.05 to 10%. most preferably 0.05 to 5%.

The concentration of all of the electrolyte salts in which they are dissolved and used is generally preferably at least 0.3 M, more preferably at least 0.5 M, most preferably at least 0.7 M, based on the above-described nonaqueous solvents. The upper limit of the concentration is preferably not greater than 3 M, more preferably not greater than 2.5 M, most preferably not greater than 2 M.

The electrolyte solution of the present invention may be obtained, for example, by mixing the above-described nonaqueous solvents, dissolving the above-described electrolyte salts and pentafluorophenyloxy compound therein, and, if necessary, further dissolving therein at least one of a vinylene carbonate (VC), 1,3-propane sultone (PS) and a triple bond-containing compound.

In this case, it is preferred that the nonaqueous solvents, pentafluorophenyloxy compound, VC, PS, triple bond-containing compound and other additives used should be previously purified to reduce impurities as much as possible to the extent that the productivity is not considerably deteriorated.

By incorporating, for example, air or carbon dioxide in the nonaqueous electrolyte solution of the present invention, the generation of gases by decomposition of the electrolyte solution may be prevented and the battery characteristics such as long-term cycling characteristics and charging and storage properties may be improved.

As the method for incorporating (dissolving) air or carbon dioxide in the nonaqueous electrolyte solution, there may be used (1) a method in which the nonaqueous electrolyte solution is previously contacted with air or a carbon dioxide-containing gas before the solution is poured in the battery; or (2) a method in which after the solution has been poured in the battery, air or a carbon dioxide-containing gas is charged in the battery before or after sealing the battery. These methods may be used in combination. It is preferred that the moisture content of the air or carbon dioxide-containing gas is as low as possible and that the air or carbon dioxide-containing gas has a dew point of $-40°$ C. or below, particularly preferably $-50°$ C. or below.

In the present invention, it is particularly preferable to use a nonaqueous electrolyte solution in which carbon dioxide is dissolved from the standpoint of improved charging and discharging characteristics at high temperatures. The amount of carbon dioxide dissolved is preferably at least 0.001% by weight, more preferably at least 0.05% by weight, still more preferably at least 0.2% by weight, based on the weight of the nonaqueous electrolyte solution. It is most preferable to dissolve carbon dioxide in the nonaqueous electrolyte solution up to the saturation concentration.

In the nonaqueous electrolyte solution of the present invention, safety of the battery in the case of overcharging can be ensured by further incorporating an aromatic compound thereinto.

As such an aromatic compound, there may be mentioned, for example, the following (a) to (c):
(a) cyclohexylbenzene, a fluorocyclohexylbenzene compound (1-fluoro-2-cyclohexylbenzene, 1-fluoro-3-cyclohexylbenzene, 1-fluoro-4-cyclohexylbenzene), biphenyl;
(b) tert-butylbenzene, 1-fluoro-4-tert-butylbenzene, tert-amylbenzene, 4-tert-butylbiphenyl, 4-tert-amylbiphenyl;
(c) terphenyls (o-, m- and p-), diphenyl ether, 2-fluorodiphenyl ether, 4-diphenyl ether, fluorobenzene, difluorobenzenes (o, m- and p-), 2-fluorobiphenyl, 4-fluorobiphenyl, 2,4-difluoroanisole, partially hydrogenated terphenyls (1,2-dicyclohexylbenzene, 2-phenylbicyclohexyl, 1,2-diphenylcyclohexane, o-cyclohexylbiphenyl).

Among these, compounds (a) and (b) are preferred. Most preferred are one or more compounds selected from cyclohexyl benzene, fluorocyclohexylbenzene compounds (1-fluoro-4-cyclohexylbenzene, etc.), tert-butylbenzene and tert-amylbenzene. A total amount of the above aromatic compounds is preferably 0.1 to 5% by weight based on the weight of the nonaqueous electrolyte solution.

[Lithium Secondary Battery]

A lithium secondary battery of the present invention comprises a positive electrode, a negative electrode and a nonaqueous electrolyte solution containing an electrolyte salt dissolved in a nonaqueous solvent. Except for the nonaqueous electrolyte solution, there are no limitations with respect to components, such as a positive electrode and a negative electrode, which are used for the secondary battery.

Thus, for example, as a positive electrode active material, a lithium compound oxide containing cobalt, manganese or nickel may be used. Only one of such positive electrode active materials may be used, or they may be used in combination of two or more thereof.

As the lithium compound oxide, there may be mentioned, for example, $LiCoO_2$, $LiMn_2O_4$, $LiNiO_2$, $LiCo_{1-x}Ni_xO_2$ ($0.01<x<1$), $LiCo_{1/3}Ni_{1/3}Mn_{1/3}O_2$ and $LiNi_{1/2}Mn_{3/2}O_4$. Further, an appropriate mixture, such as a mixture of $LiCoO_2$ with $LiMn_2O_4$, a mixture of $LiCoO_2$ and $LiNiO_2$ or a mixture of $LiMn_2O_4$ and $LiNiO_2$, may be employed. Among these, preferably used is a lithium compound oxide, such as $LiCoO_2$, $LiMn_2O_4$ or $LiNiO_2$, which can be used with a charge potential of the positive electrode in a fully charged state of at least 4.3 V based on Li. Lithium compound oxides such as $LiCo_{1/3}Ni_{1/3}Mn_{1/3}O_2$ and $LiNi_{1/2}Mn_{3/2}O_4$, which are usable at 4.4 V or higher are more preferred. The lithium compound oxides may be partly substituted with another element. For example, a part of Co of $LiCO_2$ may be substituted by Sn, Mg, Fe, Ti, Al, Zr, Cr, V, Ga, Zn, Cu or the like element.

As a positive electrode active material, a lithium-containing olivine-type phosphate may be also used. Specific examples of such a phosphate include $LiFePO_4$, $LiCoPO_4$, $LiNiPO_4$, $LiMnPO_4$ and $LiFe_{(1-x)}M_xPO_4$ (M represents at least one member selected from Co, Ni, Mn, Cu, Zn and Cd and x is $0 \leq x \leq 0.5$). Among these, $LiFePO_4$ or $LiCoPO_4$ is preferably used as a positive electrode active material for use with a high voltage.

The lithium-containing olivine-type phosphate may be used as a mixture with other positive electrode active material.

The conductive material for the positive electrode is not specifically limited as long as it is an electron conductive material which does not undergo a chemical change. Examples of the conductive material include graphites, such as natural graphite (scaly graphite, etc.) and artificial graphite, and carbon blacks, such as acetylene black, Ketjen black, channel black, furnace black, lamp black and thermal black. The graphites and carbon blacks may be used as an appropriate mixture. The amount of the conductive material added to the positive electrode mixture is preferably 1 to 10% by weight, particularly preferably 2 to 5% by weight.

The positive electrode may be manufactured by mixing a positive electrode active material, a conductive material such as acetylene black and carbon black, and a binder such as polytetrafluoroethylene, polyvinylidene fluoride, a styrene-butadiene copolymer, an acrylonitrile-butadiene copolymer, carboxymethyl cellulose and an ethylene-propylene-diene terpolymer, kneading the above mixture together with a high boiling point solvent such as 1-methyl-2-pyrrolidone to obtain a positive electrode mixture, rolling the positive electrode material on a collector such as an aluminum foil or a lath board made of a stainless steel, and then subjected the resulting assembly to a heat treatment at a temperature of about 50 to 250° C. for about 2 hours under vacuum.

As the negative electrode (negative electrode active material), there may be used a lithium metal, a lithium alloy or a material capable of occluding and releasing lithium, such as a carbon material (thermally decomposed carbon materials, cokes, graphites (such as artificial graphite and natural graphite), fired organic polymer bodies, and carbon fibers), tin or a tin compound and silicon or a silicon compound. These materials may be used singly or in combination of two or more thereof.

Above all, a carbon material is preferred. More preferred is a carbon material having a graphite crystal structure in which the (002)-plane spacing ($d_{002}$) is not greater than 0.340 nm, more preferably 0.335 to 0.340 nm.

The negative electrode may be manufactured in the same manner as the method for the manufacture of the above-described positive electrode using similar to that of the binder and the high boiling point solvent described above.

In the present invention, it is preferable to increase an electrode mixture density of the battery so as to increase the effect of addition of the pentafluorophenyloxy compound represented by the general formula (II) or (III). In particular, the density of the positive electrode (layer of a positive electrode mixture) formed on an aluminum foil is preferably at least 3.2 g/cm$^3$, more preferably at least 3.3 g/cm$^3$, most preferably at least 3.4 g/cm$^3$. It is occasionally practically difficult to manufacture an electrode with a density in excess of 4.0 g/cm$^3$. Thus, the upper limit of the density is preferably not greater than 4.0 g/cm$^3$, more preferably not greater than 3.9 g/cm$^3$, most preferably not greater than 3.8 g/cm$^3$.

The density of the negative electrode (layer of a negative electrode mixture) formed on a copper foil is preferably at least 1.3 g/cm$^3$, more preferably at least 1.4 g/cm$^3$, most preferably at least 1.5 g/cm$^3$. It is occasionally practically difficult to manufacture an electrode with a density in excess of 2.0 g/cm$^3$. Thus, the upper limit of the density is preferably not greater than 2.0 g/cm$^3$, more preferably not greater than 1.9 g/cm$^3$, most preferably not greater than 1.8 g/cm$^3$.

When the thickness of the electrode material layer is excessively small, the amount of the active material in the electrode material layer is decreased and, thus, the battery capacity is lowered. Therefore, the thickness of the electrode layer of the positive electrode (per one side of the collector) is preferably at least 30 μm, more preferably at least 50 μm. On the other hand, when the thickness is excessively large, the cycling property in the charging and discharging and rate characteristics are undesirably lowered. Thus, the thickness of the electrode layer of the positive electrode is preferably not greater than 120 μm, more preferably not greater than 100 μm.

When the thickness of the electrode layer of the negative electrode (per one side of the collector) is excessively small, the amount of the active material in the electrode material layer is decreased and, thus, the battery capacity is lowered. Therefore, the thickness is preferably at least 1 μm, more preferably at least 3 μm. On the other hand, when the thickness is excessively large, the cycling property in the charging and discharging and rate characteristics are undesirably lowered. Thus, the thickness of the electrode layer of the negative electrode is preferably not greater than 100 μm, more preferably not greater than 70 μm.

There are no specific limitations with respect to the structure of the lithium secondary battery. The secondary battery may be a coin-shaped battery, a cylindrical battery, a square-shaped battery or a laminate-type battery, having a single layered or multi-layered separator.

As a separator for batteries, there can be used a single layered or laminated porous film, woven fabric or non-woven fabric of a polyolefin such as polypropylene or polyethylene.

When a Gurley value (air permeability) of separator for batteries is excessively high, the lithium ion conductivity is lowered and, therefore, the function thereof as a battery separator is insufficient, though it may vary depending upon the manufacturing conditions. Thus, the Gurley value is preferably not greater than 1000 seconds/100 cc, more preferably not greater than 800 seconds/100 cc, most preferably not greater than 500 seconds/100 cc. On the other hand, too low a Gurley value causes a reduction of the mechanical strength. The Gurley value is, therefore, preferably at least 50 seconds/100 cc, more preferably at least 100 seconds/100 cc, most preferably at least 300 seconds/100 cc. The porosity of the separator is preferably 30 to 60%, more preferably 35 to 55%, most preferably 40 to 50% for reasons of improved capacity characteristics of the battery.

The thickness of the separator for batteries is preferably 50 μm or less, more preferably 40 μm or less, most preferably 25 μm or less, since a higher energy density is obtainable as the thickness is thin. From the standpoint of the mechanical strengths, the thickness is preferably at least 5 μm, more preferably at least 10 μm, most preferably at least 15 μm.

The lithium secondary battery of the present invention shows a good cycling property for a long period of time even when the end of charge voltage is 4.2 V or higher, particularly 4.3 V or higher. Further, the good cycle property can be maintained even when the end of charge voltage is 4.4 V. The end of discharge voltage can be set to 2.5 V or higher, and further to 2.8 V or higher. There is no specific limitation with respect to a current value, but a constant current of 0.1 to 3 C is generally utilized. The lithium secondary battery of the present invention may be charged and discharged at 40° C. to 100° C., preferably 0 to 80° C.

To cope with an increase of the internal pressure of the lithium secondary battery of the present invention, a relief valve may be provided on a sealing plate. Else, there may be adopted a method in which a cut is formed in a battery can, a gasket and other component parts.

In the present invention, a plural number of the lithium secondary batteries may be accommodated in a battery pack in series or in parallel, as necessary. Such a battery pack may be provided with a supercurrent prevention element, such as a PTC element, a temperature fuse or a bimetal, as well as a safety circuit (a circuit having a function of monitoring the voltage, temperature and current of each battery and/or whole packed batteries and shutting off the current).

EXAMPLES

The present invention is described below with reference to Examples and Comparative Examples concerning cylindrical batteries. It should be noted, however, that the present invention is not limited to these Examples, in particular, to the combinations of solvents, etc.

Example 1

Synthesis of Pentafluorophenyl Methyl Oxalate

In 35 ml of toluene, 10 g (54 mmol) of pentafluorophenol and 5 ml (61 mmol) of pyridine were dissolved. To the solution, 7.2 g (59 mmol) of methyl chloroglyoxylate were added dropwise under an ice bath for the reaction. After 1 hour stirring at room temperature, the reaction mixture was filtered and concentrated. The thus obtained crude product was purified by distillation to obtain 10.1 g of pentafluorophenyl methyl oxalate. The compound had a melting point of 34 to 35° C.

The thus obtained pentafluorophenyl methyl oxalate was subjected to a mass spectrometric analysis (using model M80B manufactured by Hitachi Ltd.) and an infrared spectroscopic analysis (IR) (using model FTS7000E manufactured by Varian Inc., USA) for the confirmation of its structure. The results are as follows:

(1) Mass spectrometric analysis: CI-MS, m/e=271 (M+1)

(2) IR: 1805, 1766, 1522, 1308, 1149, 1123, 999 cm$^{-1}$

Example 2

Synthesis of Pentafluorophenyl Ethyl Oxalate

In 50 ml of toluene, 16.5 g (90 mmol) of pentafluorophenol and 8 ml (99 mmol) of pyridine were dissolved. To the solution, 12.9 g (94 mmol) of ethyl chloroglyoxylate were added dropwise under an ice bath for the reaction. After 1 hour stirring at room temperature, the reaction mixture was filtered and concentrated. The thus obtained crude product was refined by distillation to obtain 13.5 g of pentafluorophenyl ethyl oxalate (colorless liquid). The compound had a melting point of 70 to 71° C./2 mmHg.

The thus obtained pentafluorophenyl ethyl oxalate was subjected to a mass spectrometric analysis and IR in the same manner as that in Example 1 for the confirmation of its structure. The results are as follows:

(1) Mass spectrometric analysis: CI-MS, m/e=285 (M+1)

(2) IR: 2992, 1805, 1761, 1521, 1473, 1305, 1149, 1122, 991, 859 cm$^{-1}$

Example 3

Synthesis of 2-propynyl Pentafluorophenyl Oxalate

In 100 ml of methylene chloride were dissolved 10 g (79 mmol) of oxalyl chloride, to which a solution of 4.4 g (79 mmol) of propargyl alcohol and 6.4 ml (79 mmol) of pyridine dissolved in 30 ml of methylene chloride was slowly added dropwise over 1 hour with cooling with ice. The resulting mixture was stirred for 30 minutes at room temperature to produce propynyl chloroglyoxylate in the reaction system. Subsequently, a solution of 14.5 g (79 mmol) of pentafluorophenol and 6.4 ml (79 mmol) of pyridine dissolved in 30 ml of methylene chloride was slowly added dropwise to the reaction system with cooling with ice. The resulting mixture was stirred for 1 hour at room temperature and then filtered, washed with water, dried over anhydrous magnesium sulfate and concentrated. The thus obtained crude product was purified by crystallization to obtain 2.1 g of 2-propynyl pentafluorophenyl oxalate.

The 2-propynyl pentafluorophenyl oxalate obtained was analyzed by $^1$H-NMR (using model AL300 manufactured by JEOL Ltd.) and IR for the confirmation of its structure. The results are as follows:

(1) $^1$H-NMR (CDCl$_3$/TMS): 2.59 ppm (s, 1H, C≡CH), 4.89 ppm (s, 2H, —CH$_2$—)

(2) IR: 3249, 1744, 1182, 943, 729, 715 cm$^{-1}$

Example 4

Synthesis of bis(pentafluorophenyl) sulfite

In 35 ml of toluene, 10 g (54 mmol) of pentafluorophenol and 5 ml (61 mmol) of pyridine were dissolved. To the solution, 3.3 g (28 mmol) of thionyl chloride were added dropwise under an ice bath for the reaction. The product was purified by distillation to obtain 7.6 g of bis(pentafluoropheny) sulfite (colorless liquid). The compound had a boiling point of 95 to 95.5° C./2 mmHg.

The thus obtained bis(pentafluoropheny) sulfite was subjected to a mass spectrometric analysis and IR in the same manner as that in Example 1 for the confirmation of its structure. The results are as follows:

(1) Mass spectrometric analysis: CI-MS, m/e=415 (M+1)

(2) IR: 1517, 1467, 1313, 1252, 1140, 997, 984 cm$^{-1}$

Example 5

Synthesis of 2-propynyl Pentafluorophenyl Carbonate

In 100 ml of methylene chloride were dissolved 7.3 g (25 mmol) of triphosgene, to which a solution of 4.2 g (74 mmol) of propargyl alcohol and 6.0 ml (74 mmol) of pyridine dissolved in 30 ml of methylene chloride was slowly added dropwise over 1 hour with cooling with ice. The resulting mixture was stirred for 30 minutes at room temperature to produce propynyl chloroformate in the reaction system. Subsequently, a solution of 13.7 g (74 mmol) of pentafluorophenol and 6.0 ml (74 mmol) of pyridine dissolved in 30 ml of methylene chloride was slowly added dropwise to the reaction system with cooling with ice. The resulting mixture was stirred for 1 hour at room temperature and then filtered, washed with water, dried over anhydrous magnesium sulfate and concentrated. The thus obtained crude product was purified by crystallization to obtain 7.5 g of 2-propynyl pentafluorophenyl carbonate. The compound had a melting point of 66 to 67° C.

The thus obtained 2-propynyl pentafluorophenyl carbonate was subjected to a mass spectrometric analysis and IR in the same manner as that in Example 1 for the confirmation of its structure. The results are as follows:

(1) Mass spectrometric analysis: CI-MS, m/e=267 (M+1)

(2) IR: 3286, 1783, 1524, 1439, 1377, 1278, 1234, 1162, 1007, 993, 977, 941, 910, 774, 723, 659 cm$^{-1}$

Example 6

Preparation of Nonaqueous Electrolyte Solution

A nonaqueous solvent of ethylene carbonate (EC):vinylene carbonate (VC):methyl ethyl carbonate (MEC)=30:2:68 (volume ratio) was prepared in the atmosphere of dry nitrogen. In this solvent LiPF$_6$ and LiBF$_4$ as electrolyte salts were dissolved to concentrations of 0.95 M and 0.05 M, respectively to obtain a nonaqueous electrolyte solution. To the nonaqueous electrolyte solution was further added pentafluorophenyl methyl oxalate to a concentration of 1% by weight.

[Manufacture of Lithium Secondary Battery]

Ninety-four percent by weight of $LiNi_{1/3}Mn_{1/3}Co_{1/3}O_2$ (positive electrode active material), 3% by weight of acetylene black (conductive material) and 3% by weight of polyvinylidene fluoride (binder) were mixed, to which 1-methyl-2-pyrrolidone as a solvent was further added and mixed. The resulting mixture was applied onto an aluminum foil, dried, compression molded and heat treated to prepare a positive electrode.

On the other hand, 95% by weight of artificial graphite (negative electrode active material) having a graphite type crystal structure with a (002)-plane spacing ($d_{002}$) of 0.335 nm were mixed with 5% by weight of polyvinylidene fluoride (binder), to which 1-methyl-2-pyrrolidone as a solvent was further mixed. The resulting mixture was applied onto a copper foil, dried, compression molded and heat treated to prepare a negative electrode.

A cylindrical battery of an 18650 size (diameter: 18 mm, height: 65 mm) was then manufactured by using a microporous polyethylene film separator, pouring the above nonaqueous electrolyte solution and then trapping carbon dioxide having a dew point of −60° C. up to the saturation concentration before sealing the battery. The battery was provided with a pressure release vent and an internal current breaking device (PTC element). At this time, the positive electrode had an electrode density of 3.5 g/cm³, while the negative electrode had an electrode density of 1.6 g/cm³. The electrode layer of the positive electrode had a thickness (per one side of the collector) of 70 μm, while the electrode layer of the negative electrode had a thickness (per one side of the collector) of 60 μm.

[Measurement of Battery Characteristics]

The thus obtained 18650 battery was charged at a constant electric current of 2.2 A (1 C) at ambient temperature (25° C.) to a voltage of 4.2 V. The charging was thereafter continued for 3 hours in total under a constant voltage with a terminal voltage of 4.2 V. Next, the battery was discharged at a constant electric current of 2.2 A (1 C) to a terminal voltage of 3.0 V. The charge-discharge cycle was repeated. The initial charging and discharging capacity was almost the same as that of a case in which 0.95 M $LiPF_6$+0.05M $LiBF_4$–EC:VC:MEC=30:2:68 (volume ratio) was used as a nonaqueous electrolyte solution (Comparative Example 1) with no pentafluorophenyl methyl oxalate being added thereto. The battery characteristics after 300 cycles were measured to reveal that the discharge capacity retentivity, when the initial discharge capacity was 100%, was about 81%. The conditions for the preparation of the battery and the battery characteristics thereof are summarized in Table 1.

Example 7

In the same manner as that in Example 6, a cylindrical battery was manufactured and the battery characteristics were measured except that 2-propynylpentafluorophenyl oxalate was used in place of pentafluorophenylmethyl oxalate. The results are shown in Table 1.

Example 8

In the same manner as that in Example 6, a cylindrical battery was manufactured and the battery characteristics were measured except that bis(pentafluorophenyl) sulfite was used in place of pentafluorophenyl methyl oxalate. The results are shown in Table 1.

Example 9

In the same manner as that in Example 6, a cylindrical battery was manufactured and the battery characteristics were measured except that 2-propynylpentafluorophenyl carbonate was used in place of pentafluorophenyl methyl oxalate. The results are shown in Table 1.

Example 10

In the same manner as that in Example 6, a cylindrical battery was manufactured and the battery characteristics were measured except that bis(pentafluorophenyl) oxalate was used in place of pentafluorophenyl methyl oxalate in an amount of 0.1% by weight based on the nonaqueous electrolyte solution. The results are shown in Table 1.

Example 11

In the same manner as that in Example 6, a cylindrical battery was manufactured and the battery characteristics were measured except that the amount of pentafluorophenyl methyl oxalate was changed to 0.5% by weight and that methy propargyl carbonate was further added in an amount of 0.5% by weight. The results are shown in Table 1.

Comparative Example 1

In the same manner as that in Example 6, a cylindrical battery was manufactured and the battery characteristics were measured except that the pentafluorophenyl methyl oxalate was not added. The results are shown in Table 1.

Comparative Examples 2 and 3

In the same manner as that in Example 6, cylindrical batteries were manufactured and the battery characteristics were measured except that the compounds shown in Table 1 were used each in place of the pentafluorophenyl methyl oxalate. The results are shown in Table 1.

Example 12

In the same manner as that in Example 6, a cylindrical battery was manufactured and the battery characteristics were measured except that a nonaqueous electrolyte solution was prepared by dissolving $LiPF_6$ and $LiBF_4$ as electrolyte salts to concentrations of 0.95 M and 0.05 M, respectively, in a nonaqueous solvent of ethylene carbonate (EC):1,3-propane sultone (PS):methyl ethyl carbonate (MEC)=30:2:68 (volume ratio) prepared in a dry nitrogen atmosphere and that pentafluorophenyl ethyl oxalate was used for the nonaqueous electrolyte solution. The results are shown in Table 1.

Example 13

In the same manner as that in Example 12, a cylindrical battery was manufactured and the battery characteristics were measured except that lithium pentafluorophenoxide was used in an amount of 0.05% by weight in place of the pentafluorophenyl ethyl oxalate. The results are shown in Table 1.

Comparative Example 4

In the same manner as that in Example 12, a cylindrical battery was manufactured and the battery characteristics were measured except that pentafluorophenyl ethyl oxalate was not added. The results are shown in Table 1.

TABLE 1

|  |  | Compound (amount added: wt %) | Composition of electrolyte solution (volume ratio) | 300 cycle Discharge capacity retentivity (%) |
|---|---|---|---|---|
| Example | 6 | Pentafluorophenyl methyl oxalate (1) | 0.95M LiPF$_6$ + 0.05M LiBF$_4$ EC/VC/MEC = 30/2/68 | 81 |
|  | 7 | 2-Propynyl pentafluorophenyl oxalate (1) | 0.95M LiPF$_6$ + 0.05M LiBF$_4$ EC/VC/MEC = 30/2/68 | 82 |
|  | 8 | Bis(pentafluorophenyl) sulfite (1) | 0.95M LiPF$_6$ + 0.05M LiBF$_4$ EC/VC/MEC = 30/2/68 | 81 |
|  | 9 | 2-Propynyl pentafluorophenyl carbonate (1) | 0.95M LiPF$_6$ + 0.05M LiBF$_4$ EC/VC/MEC = 30/2/68 | 82 |
|  | 10 | Bis(pentafluorophenyl) oxalate (0.1) | 0.95M LiPF$_6$ + 0.05M LiBF$_4$ EC/VC/MEC = 30/2/68 | 80 |
|  | 11 | Pentafluorophenyl methyl oxalate (0.5) + Methyl propargyl carbonate (0.5) | 0.95M LiPF$_6$ + 0.05M LiBF$_4$ EC/VC/MEC = 30/2/68 | 83 |
|  | 12 | Pentafluorophenyl ethyl oxalate (1) | 0.95M LiPF$_6$ + 0.05M LiBF$_4$ EC/PS/MEC = 30/2/68 | 80 |
|  | 13 | Lithium pentafluorophenoxide (0.05) | 0.95M LiPF$_6$ + 0.05M LiBF$_4$ EC/PS/MEC = 30/2/68 | 79 |
| Comparative Example | 1 | None (0) | 0.95M LiPF$_6$ + 0.05M LiBF$_4$ EC/VC/MEC = 30/2/68 | 71 |
|  | 2 | 2-Propynylphenyl oxalate (1) | 0.95M LiPF$_6$ + 0.05M LiBF$_4$ EC/VC/MEC = 30/2/68 | 73 |
|  | 3 | 2-Propynylphenyl carbonate (1) | 0.95M LiPF$_6$ + 0.05M LiBF$_4$ EC/VC/MEC = 30/2/68 | 72 |
|  | 4 | None (0) | 0.95M LiPF$_6$ + 0.05M LiBF$_4$ EC/PS/MEC = 30/2/68 | 70 |

Remark 1: The initial charging and discharging capacity in Examples 6 to 11 were nearly the same as that in Comparative Example 1

Remark 2: The initial charging and discharging capacity in Examples 12 and 13 were nearly the same as that in Comparative Example 4

It will be appreciated that the lithium secondary batteries of above Examples have superior long-term cycling property and charge retention characteristics as compared with the lithium secondary batteries of Comparative Examples which do not contain a pentafluorophenyloxy compound represented by the general formula (II) or (III).

INDUSTRIAL APPLICABILITY

According to the present invention there can be provided a novel pentafluorophenyloxy compound useful as an intermediate raw material for medicaments, agricultural chemicals, electronic materials, polymeric materials, etc and as a battery material and a method for producing same.

Further, by incorporating a pentafluorophenyloxy compound represented by the above general formula (II) or (III) in a nonaqueous electrolyte solution as an additive, a lithium secondary battery having excellent battery characteristics such as electrical capacity, cycling property and storage property and capable of exhibiting the excellent battery characteristics for a long period of time.

The invention claimed is:

1. A nonaqueous electrolyte solution, in which an electrolyte salt is dissolved in a nonaqueous solvent, the nonaqueous electrolyte solution comprising a pentafluorophenyloxy compound in an amount of 0.01 to 10% by weight based on the weight of the nonaqueous electrolyte solution, the pentafluorophenyloxy compound being represented by the following formula (II):

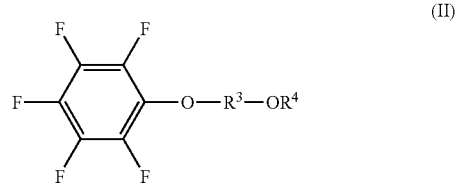

(II)

wherein R$^3$ represents a —COCO— group, a C=O group, a S=O group or a S(=O)$_2$ group, R$^4$ represents a C$_1$ to C$_{12}$ alkyl group, a C$_3$ to C$_{12}$ cycloalkyl group, a C$_2$ to C$_{12}$ alkenyl group, a C$_3$ to C$_{12}$ alkynyl group, a C$_6$ to C$_{18}$ aryl group or a C$_7$ to C$_{20}$ aralkyl group wherein at least one of the hydrogen atoms of R$^4$ may optionally be substituted with a halogen atom, with the proviso that R$^4$ represents a C$_2$ to C$_{12}$ alkenyl group or a C$_3$ to C$_{12}$ alkynyl group when R$^3$ represents a C=O group.

2. The nonaqueous electrolyte solution as defined in claim 1, wherein the nonaqueous solvent contains a cyclic carbonate and a linear carbonate.

3. The nonaqueous electrolytic solution as defined in claim 2, wherein the nonaqueous solvent comprises a cyclic carbonate comprising at least one member selected from the group consisting of ethylene carbonate, propylene carbonate, butylene carbonate, fluoroethylene carbonate, dimethylvinylene carbonate, vinyl ethylene carbonate, and a linear carbonate, and the volume ratio of the cyclic carbonate to the linear carbonate is 20:80 to 40:60.

4. The nonaqueous electrolyte solution as defined in claim 1 or 2, wherein the nonaqueous solvent further contains at least one member selected from the group consisting of vinylene carbonate, 1,3-propane sultone and compounds having a triple bond.

5. The nonaqueous electrolytic solution as defined in claim 1 or 2, wherein the electrolyte salts comprises at least one member selected from the group consisting of $LiPF_6$, $LiBF_4$ and $LiN(SO_2CF_3)_2$.

6. The nonaqueous electrolytic solution as defined in claim 1, wherein the pentafluorophenyloxy compound represented by the formula (II) is at least one member selected from the group consisting of 2-propynyl pentafluorophenyl carbonate, 2-butynyl pentafluorophenyl carbonate, 3-butynyl pentafluorophenyl carbonate and 4-pentynyl pentafluorophenyl carbonate.

7. The nonaqueous electrolytic solution as defined in claim 1 or 2, wherein the nonaqueous electrolyte solution comprises at least one member selected from the group consisting of vinylene carbonate, 1,3-propane sultone and a triple bond-containing compound comprising at least one of methyl propargyl carbonate, ethyl propargyl carbonate, dipropargyl carbonate, dipropargyl oxalate, propargyl methanesulfonate, dipropargyl sulfite, methylpropargyl sulfite and ethyl propargyl sulfite, in which the content of vinylene carbonate, 1,3-propane sultone and triple bond-containing compound are 0.01 to 10% by weight respectively based on the volume of the nonaqueous electrolyte solution.

8. The nonaqueous electrolytic solution as defined in claim 1, wherein the nonaqueous electrolyte solution comprises a pentafluorophenyloxy compound represented by the following formula (II):

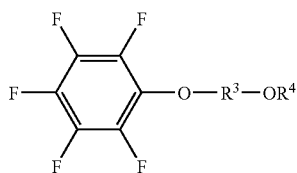

(II)

wherein $R^3$ represents a C=O group; and
$R^4$ represents a $C_2$ to $C_{12}$ alkenyl group or a $C_3$ to $C_{12}$ alkynyl group.

9. A lithium secondary battery comprising a positive electrode, a negative electrode, and a nonaqueous electrolyte solution which includes an electrolyte salt dissolved in a nonaqueous solvent, the nonaqueous electrolyte solution comprising a pentafluorophenyloxy compound in an amount of 0.01 to 10% by weight based on the weight of the nonaqueous electrolyte solution, the pentafluorophenyloxy compound being represented by the following formula (II):

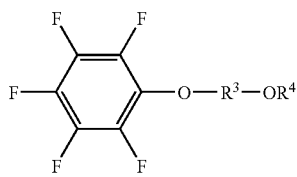

(II)

wherein $R^3$ represents a —COCO— group, a C=O group, a S=O group or a $S(=O)_2$ group, $R^4$ represents a $C_1$ to $C_{12}$ alkyl group, a $C_3$ to $C_{12}$ cycloalkyl group, a $C_2$ to $C_{12}$ alkenyl group, a $C_3$ to $C_{12}$ alkynyl group, a $C_6$ to $C_{18}$ aryl group or a $C_7$ to $C_{20}$ aralkyl group wherein at least one of the hydrogen atoms of $R^4$ may optionally be substituted with a halogen atom, with the proviso that $R^4$ represents a $C_2$ to $C_{12}$ alkenyl group or a $C_3$ to $C_{12}$ alkynyl group when $R^3$ represents a C=O group.

10. The lithium secondary battery as defined in claim 9, wherein the positive electrode comprises lithium compound oxides containing at least one member selected from the group consisting of cobalt, manganese and nickel as a positive electrode active material.

11. The lithium secondary battery as defined in claim 9, wherein the negative electrode comprises at least one member selected from the group consisting of thermally decomposed carbon materials, cokes, graphites, fired organic polymer bodies and carbon fibers as negative electrode active material.

12. A nonaqueous electrolyte solution, in which an electrolyte salt is dissolved in a nonaqueous solvent, the nonaqueous electrolyte solution comprising a pentafluorophenyloxy compound in an amount of 0.01 to 10% by weight based on the weight of the nonaqueous electrolyte solution, the pentafluorophenyloxy compound being represented by the following formula (II):

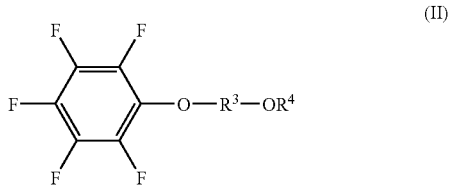

(II)

wherein $R^3$ represents a —COCO— group, a S=O group or a $S(=O)_2$ group, $R^4$ represents a $C_1$ to $C_{12}$ alkyl group, a $C_3$ to $C_{12}$ cycloalkyl group, a $C_2$ to $C_{12}$ alkenyl group, a $C_3$ to $C_{12}$ alkynyl group, a $C_6$ to $C_{18}$ aryl group or a $C_7$ to $C_{20}$ aralkyl group, wherein, optionally, at least one of the hydrogen atoms of $R^4$ may be substituted with a halogen atom.

13. A lithium secondary battery comprising a positive electrode, a negative electrode, and a nonaqueous electrolyte solution which includes an electrolyte salt dissolved in a nonaqueous solvent, the nonaqueous electrolyte solution comprising a pentafluorophenyloxy compound in an amount of 0.01 to 10% by weight based on the weight of the nonaqueous electrolyte solution, the pentafluorophenyloxy compound being represented by the following formula (II):

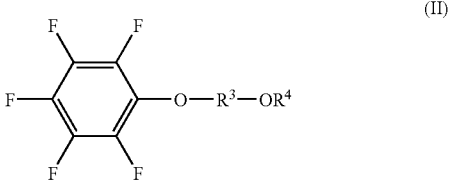

(II)

wherein $R^3$ represents a —COCO— group, a S=O group or a $S(=O)_2$ group, $R^4$ represents a $C_1$ to $C_{12}$ alkyl group, a $C_3$ to $C_{12}$ cycloalkyl group, a $C_2$ to $C_{12}$ alkenyl group, a $C_3$ to $C_{12}$ alkynyl group, a $C_6$ to $C_{18}$ aryl group or a $C_7$ to $C_{20}$ aralkyl group, wherein, optionally, at least one of the hydrogen atoms of $R^4$ may be substituted with a halogen atom.

14. A nonaqueous electrolyte solution, in which an electrolyte salt is dissolved in a nonaqueous solvent, the nonaqueous electrolyte solution comprising a pentafluorophenyloxy compound in an amount of 0.01 to 10% by weight based on the weight of the nonaqueous electrolyte solution, the pentafluorophenyloxy compound being represented by the following formula (II):

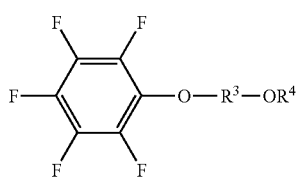

(II)

wherein $R^3$ represents a —COCO— group, a C=O group, a S=O group or a S(=O)$_2$ group, $R^4$ represents a $C_1$ to $C_{12}$ alkyl group, a $C_3$ to $C_{12}$ cycloalkyl group, a $C_2$ to $C_{12}$ alkenyl group, a $C_3$ to $C_{12}$ alkynyl group, a $C_6$ to $C_{18}$ aryl group or a $C_7$ to $C_{20}$ aralkyl group wherein at least one of the hydrogen atoms of $R^4$ may optionally be substituted with a halogen atom, with the proviso that $R^4$ represents a $C_2$ to $C_{12}$ alkenyl group or a $C_3$ to $C_{12}$ alkynyl group when $R^3$ represents a —COCO— group, a S=O group, or a S(=O)$_2$ group.

* * * * *

UNITED STATES PATENT AND TRADEMARK OFFICE
CERTIFICATE OF CORRECTION

PATENT NO. : 7,794,876 B2 Page 1 of 1
APPLICATION NO. : 11/632840
DATED : September 14, 2010
INVENTOR(S) : Koji Abe et al.

It is certified that error appears in the above-identified patent and that said Letters Patent is hereby corrected as shown below:

On the title page, Item (86), should read:

-- (86) PCT No.: PCT/JP2006/322285

§ 371 (c)(1),
(2), (4) Date: Mar. 1, 2007 --

Signed and Sealed this

Ninth Day of November, 2010

David J. Kappos
*Director of the United States Patent and Trademark Office*